(12) United States Patent
Wu et al.

(10) Patent No.: US 8,734,513 B2
(45) Date of Patent: May 27, 2014

(54) ARTIFICIAL RETINAL SYSTEM AND RETINAL IMPLANT CHIP THEREOF

(75) Inventors: Chun-Yu Wu, Hsinchu (TW); Po-Kang Lin, Taipei (TW); Chuan-Chin Chiao, Taipei (TW); Jui-Wen Pan, Hsinchu (TW); Wen-Chia Yang, Hsinchu County (TW)

(73) Assignee: National Chiao Tung University, Hsinchu (TW)

( * ) Notice: Subject to any disclaimer, the term of this patent is extended or adjusted under 35 U.S.C. 154(b) by 0 days.

(21) Appl. No.: 13/586,063

(22) Filed: Aug. 15, 2012

(65) Prior Publication Data

US 2013/0218271 A1  Aug. 22, 2013

(30) Foreign Application Priority Data

Feb. 16, 2012  (TW) .............................. 101105086 A

(51) Int. Cl.
*A61F 2/16*  (2006.01)

(52) U.S. Cl.
USPC .......................................... 623/6.63; 607/54

(58) Field of Classification Search
USPC .......................................... 623/6.63; 607/54
See application file for complete search history.

(56) References Cited

U.S. PATENT DOCUMENTS

| 5,653,751 A | * | 8/1997 | Samiy et al. .................. 623/6.63 |
| 7,622,702 B2 | | 11/2009 | Wu et al. |
| 7,751,896 B2 | * | 7/2010 | Graf et al. ........................ 607/54 |
| 2002/0099420 A1 | * | 7/2002 | Chow et al. ..................... 607/54 |
| 2005/0090875 A1 | | 4/2005 | Palanker et al. |
| 2008/0086206 A1 | * | 4/2008 | Nasiatka et al. ............. 623/6.14 |
| 2009/0011536 A1 | * | 1/2009 | Zhang et al. .................... 438/85 |

OTHER PUBLICATIONS

Yang, The Analysis and Design of Retinal Chips for Motion Detector and Visual Prosthesis Applications, Dissertation, Department of Electronics Engineering and Institute of Electronics, pp. 1-129, Aug. 2011.

* cited by examiner

*Primary Examiner* — Paul Prebilic
(74) *Attorney, Agent, or Firm* — Morgan, Lewis & Bockius LLP

(57) ABSTRACT

An artificial retinal system includes an external optical device having an image generator and a background light generator, and a retinal implant chip having a solar cell and a stimulus generator. The stimulus generator is disposed to receive a target image projected by the image generator and a background light provided by the background light generator, and receives the electrical power from the solar cell. The stimulus generator includes an image sensing stimulator operable to convert the target image into electrical stimuli, and a contrast enhancer for reducing effect of the background light on the electrical stimuli.

7 Claims, 6 Drawing Sheets

ARTIFICIAL RETINAL SYSTEM AND RETINAL IMPLANT CHIP THEREOF

CROSS-REFERENCE TO RELATED APPLICATION

This application claims priority to Taiwanese Application No. 101105086, filed on Feb. 16, 2012.

BACKGROUND OF THE INVENTION

1. Field of the Invention

The invention relates to a vision aid, and more particularly to an artificial retinal system and a retinal implant chip.

2. Description of the Related Art

Retinitis Pigmentosa (RP) and age-related macular degeneration (AMD) are two diseases resulting from degeneration of photoreceptors of the retina. AMD is the main cause of adult blindness in western countries. No effective treatment is available for the blindness caused by these diseases. However, an artificial retina which can replace the photoreceptors has been employed to restore vision. Conventional artificial retina includes a solar cell for receiving and converting an optical image into current to stimulate the remaining ganglion cells, such that visions of patients blinded as a result of degeneration of photoreceptors can be restored. In the prior art, insufficient power supply of the solar cell is an issue, and use of wiring and routing for providing power arises in safety concerns.

In U.S. Pat. No. 7,622,702, a divisional power supply scheme (DPSS) is disclosed to increase the output current from an image sensing pixel array. The image sensing pixel array includes a plurality of solar cells, and is divided into N blocks. Only one block is activated at a time and the blocks are activated in turns. As long as the activation frequency is over the desired frequency of persistence of vision (about 30 Hz), the patient can have a normal vision. In this scheme, assuming the current provided by the solar cell is $I_{SC}$, the current obtained by the activated block is $I_{SC}$. If all the N blocks can be activated at the same time, current obtained by each block is $I_{SC}/N$. Thus, the DPSS can increase several times the output current.

However, image projected to the image sensing pixel array may have bright and dark parts. If the image is used as both an image signal and the sole power source in the DPSS, the photocurrent generated from the dark parts shall be smaller than that generated from the bright parts. This is normal for image sensing to maintain a contrast of the image. As a solar cell, however, the lower illumination generates smaller photocurrent and smaller power, thereby resulting in unstable power supply.

US patent application publication no. US20050090875 discloses a display and projector to be worn on a head of the patient for providing sufficient light into the eyeballs, so as to increase the output current from the solar cell. The proposed scheme, however, results in lower image contrast.

SUMMARY OF THE INVENTION

Therefore, an object of the present invention is to provide an artificial retinal system capable of providing sufficient power and maintaining image contrast.

According to the present invention, an artificial retinal system comprises:

an external optical device including:
an image generator for receiving an external image, and operable to provide a target image associated with the external image and to output the target image by optical projection; and
a background light generator for providing a background light; and
a retinal implant chip including:
a solar cell to be disposed within an illumination range of the background light for receiving the background light and operable to convert the background light into electrical power; and
a stimulus generator to be disposed to receive the target image projected by the image generator and the background light provided by the background light generator, the stimulus generator being coupled to the solar cell for receiving the electrical power therefrom and including an image sensing stimulator that is operable to convert the target image into electrical stimuli, the stimulus generator further including a contrast enhancer for reducing effect of the background light received by the stimulus generator on the electrical stimuli generated by the image sensing stimulator.

BRIEF DESCRIPTION OF THE DRAWINGS

Other features and advantages of the present invention will become apparent in the following detailed description of the preferred embodiments with reference to the accompanying drawings, of which.

DETAILED DESCRIPTION OF THE PREFERRED EMBODIMENTS

Figure 1:
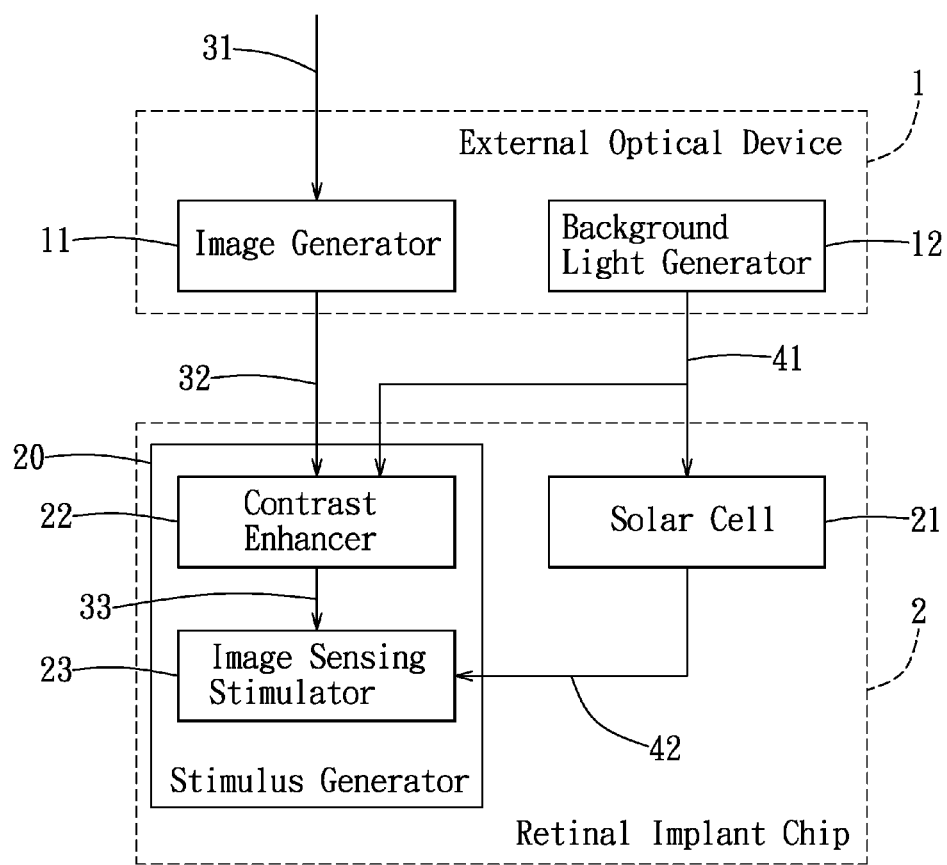
FIG. 1 is a block diagram showing a first preferred embodiment of the artificial retinal system according to the present invention.
Figure 2:
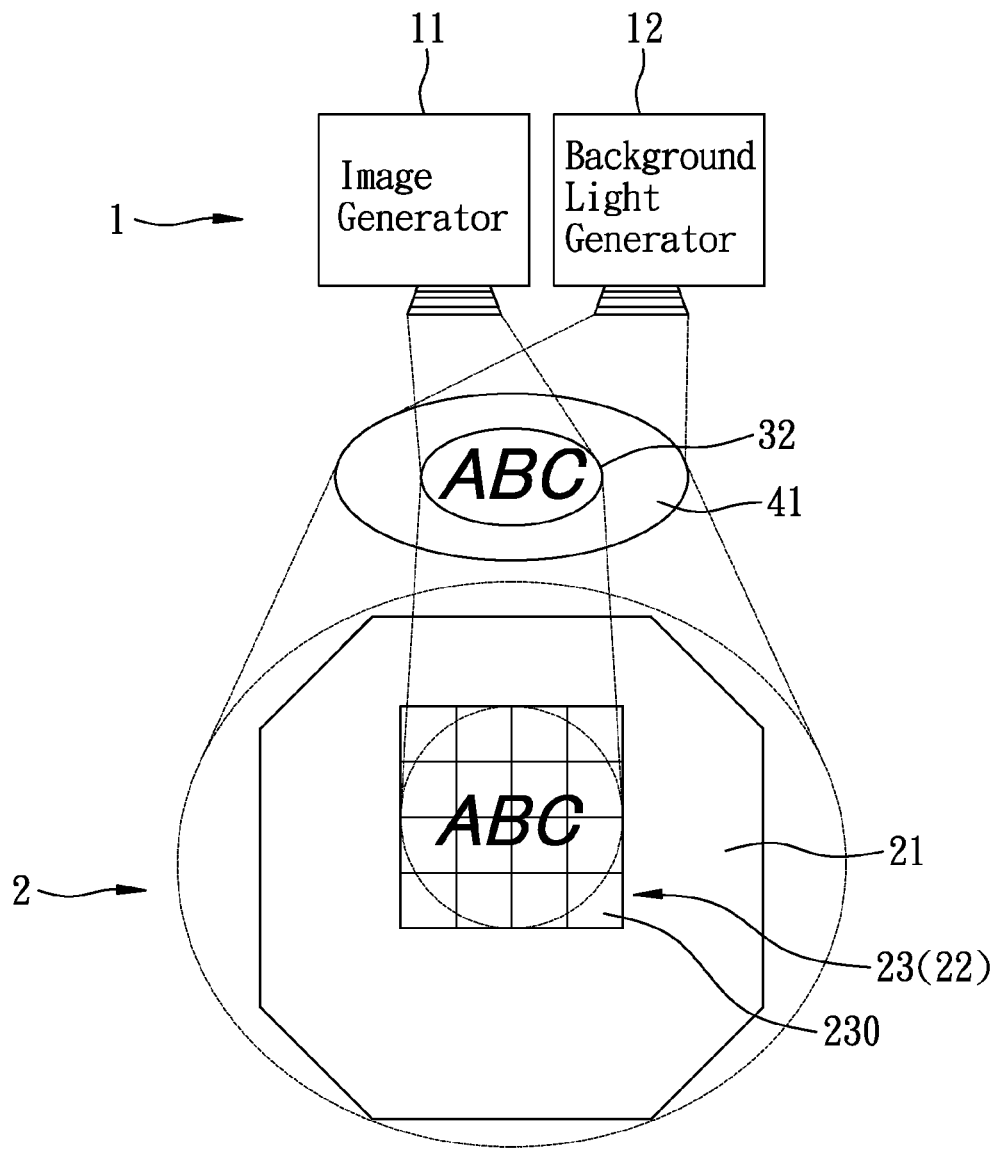
FIG. 2 is a schematic diagram showing the first preferred embodiment.

Referring to FIG. 1 and FIG. 2, the first preferred embodiment of the artificial retinal system according to this invention is shown to include an external optical device 1 and a retinal implant chip 2.

In application, the retinal implant chip 2 is an implantable biomedical chip to be disposed on a sub-retina of a patient's eyeball by surgery. The external optical device 1 includes an image generator 11 and a background light generator 12.

The image generator 11 receives an external image 31 and is operable to perform image processing so as to provide a target image 32 associated with the external image 31 and to output the target image 32 by optical projection. The external image 31 may be visible light emitted from an object. The image processing may include image enhancement, time domain processing, and spatial domain processing.

The background light generator 12 is operable to provide a background light 41 having an optical characteristic different from that of the target image 32 in this embodiment. The background light 41 is a power source of the retinal implant chip 2 in this invention.

The retinal implant chip 2 is disposed in a patient's eyeball, and includes a solar cell 21 and a stimulus generator 20.

The solar cell 21 is disposed within an illumination range of the background light 41 for receiving the background light 41 and is operable to convert the background light 41 into electrical power 42.

The stimulus generator 20 is disposed to receive the target image 32 projected by the image generator 11 and the background light 41 provided by the background light generator 12. The stimulus generator 20 is coupled to the solar cell 21 for receiving the electrical power 42 therefrom and includes an image sensing stimulator 23 that is operable to convert the target image 32 into electrical stimuli for restoring patient's vision, and further includes a contrast enhancer 22 for reducing effect of the background light received by the stimulus generator 20 on the electrical stimuli generated by the image sensing stimulator 23.

The image generator 11 and the background light generator 12 may have a respective optical device (not shown) for projection of the target image 32 to the image sensing stimulator 23 and for projection of the background light 41 to the solar cell 21. Since the chip-implantable area of a retina is only several millimeters in width, the size of the retinal implant chip 2 is limited, so that the distance between the image sensing stimulator 23 and the solar cell 21 must not be too far. In practice, precise alignment in such a small chip area is not beneficial, so that the illumination ranges of the target image 32 and the background light 41 unavoidably overlap. Referring to FIG. 2, the image sensing stimulator 23 is centered on the retinal implant chip 2 and is surrounded by the solar cell 21 in this preferred embodiment. The projected background light 41 completely covers the target image 32, so that the background light 41 is also projected on the image sensing stimulator 23, thereby producing additional photocurrent that may reduce the image contrast. The background light 41 is not a part of the desired image, and signals generated from the background light 41 are not desired to be outputted to the ganglion cells to thereby cause additional power consumption.

In the first preferred embodiment, the contrast enhancer 22 is disposed in front of the image sensing stimulator 23 with respect to the image generator 11 and within an illumination range of the target image 32 projected by the image generator 11 for allowing the target image 32 to reach the image sensing stimulator and for filtering out the background light 41 received by the stimulus generator 20 using an optical method. The wavelength of the target image 32 may be different from that of the background light 41, and the contrast enhancer 22 may be an optical filter covering the image sensing stimulator 23. The optical filter is capable of filtering out the background light 41 and allowing the target image 32 to pass therethrough, so that the background light 41 does not cause the image sensing stimulator 23 to generate substantial photocurrent. The background light 41 may be an invisible light. Infrared light is preferably used as a background light 41 since the image sensing stimulator 23 is usually made using a silicon chip, and the silicon chip has better conversion efficiency for infrared light so as to generate greater photocurrent. Another reason is that the tissue of the human eyes does not absorb infrared light, and is thus able to withstand greater intensity for infrared light. The stronger infrared light can thus be used as the light source for power supply.

Moreover, the background light 41 may have a polarization different from that of the target image 32. In this case, the contrast enhancer 22 is a polarizing filter capable of filtering the background light 41 and covering the image sensing stimulator 23.

Therefore, a substantial amount of the background light 41 does not reach the image sensing stimulator 23. In this embodiment, the image sensing stimulator 23 is coupled to the solar cell 21 for receiving the electrical power 42 therefrom, and receives the filtered image 33 through the contrast enhancer 22.

Figure 3:
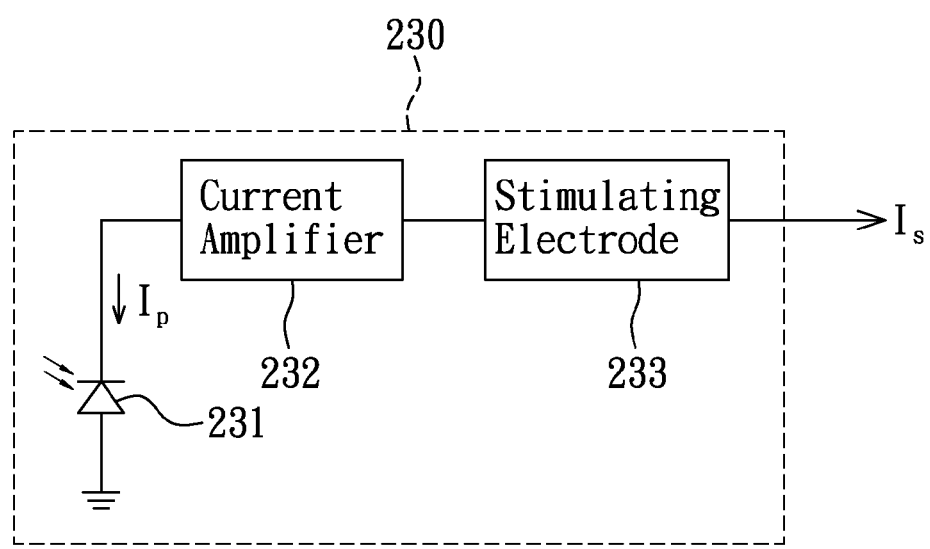
FIG. 3 is a circuit diagram illustrating a pixel of the first preferred embodiment.

Referring to FIG. 2 and FIG. 3, the image sensing stimulator 23 includes a plurality of pixels 230. Each pixel 230 includes an image sensor 231, a current amplifier 232, and a stimulating electrode 233.

The image sensor 231 is used for receiving and converting a part of the target image 32 into pixel photocurrent $I_p$.

The current amplifier 232 is coupled to the image sensor 231 for receiving and amplifying the pixel photocurrent $I_p$ therefrom.

The stimulating electrode 233 is coupled to the current amplifier 232 for receiving the pixel photocurrent $I_p$ amplified thereby to output a pixel electrical stimulus $I_s$ to stimulate a patient's ganglion cell for generation of vision. The electrical stimuli generated by the image sensing stimulator 23 are composed of the pixel electrical stimuli $I_s$ from the pixels 230.

Figure 4:
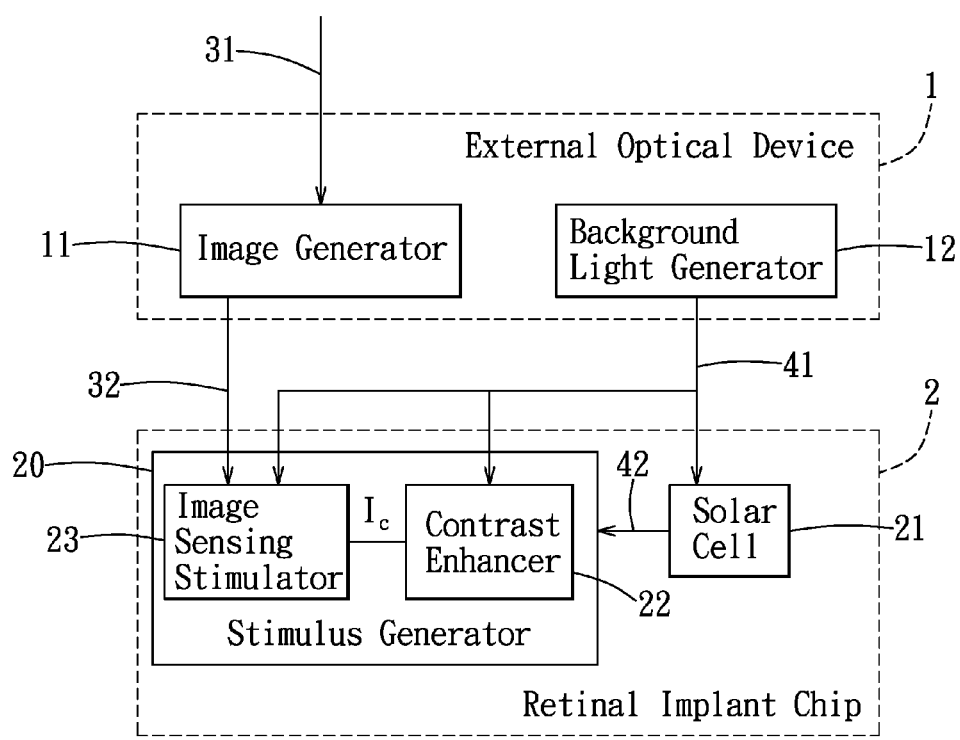
FIG. 4 is a block diagram showing a second preferred embodiment of the artificial retinal system according to the present invention.
Figure 5:
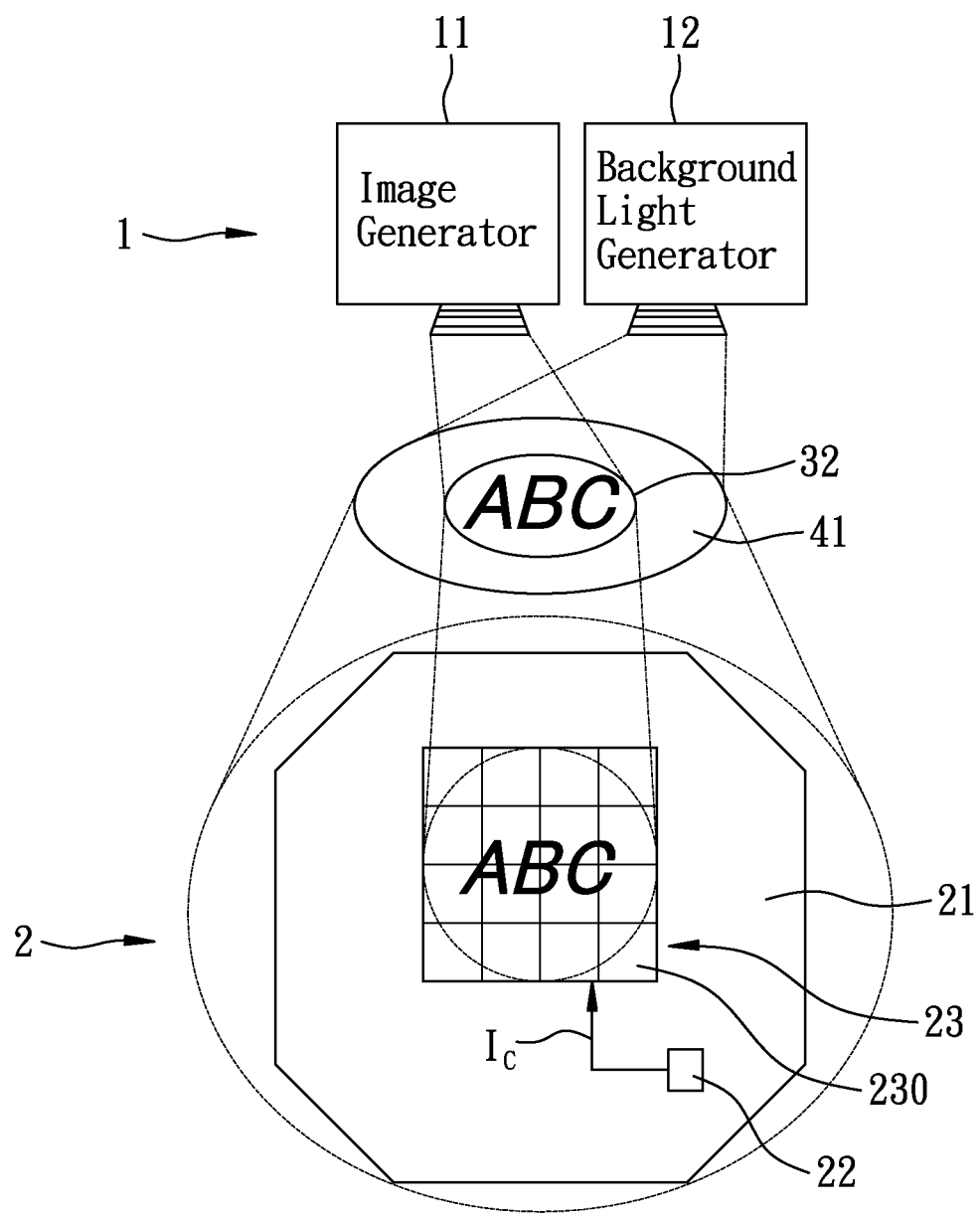
FIG. 5 is a schematic diagram showing the second preferred embodiment.

Referring to FIG. 4 and FIG. 5, the second preferred embodiment of the artificial retinal system according to this invention is shown to include an external optical device 1 and a retinal implant chip 2. In this embodiment, effect of the background light received by the stimulus generator 20 on the electrical stimuli is reduced using an electric circuit method, so that the target image 32 is allowed to have the same optical characteristics as the background light 41.

In the second preferred embodiment, the contrast enhancer 22 is disposed within the illumination range of the background light 41 for receiving the background light 41 and is operable to convert the background light 41 into correction current $I_c$.

The image sensing stimulator 23 is configured to receive and convert the target image 32 and the background light 41 into an initial electrical output, is coupled to the contrast enhancer 22 for receiving the correction current $I_c$ therefrom, and is operable to correct the initial electrical output using the correction current $I_c$ so as to generate the electrical stimuli.

Figure 6:
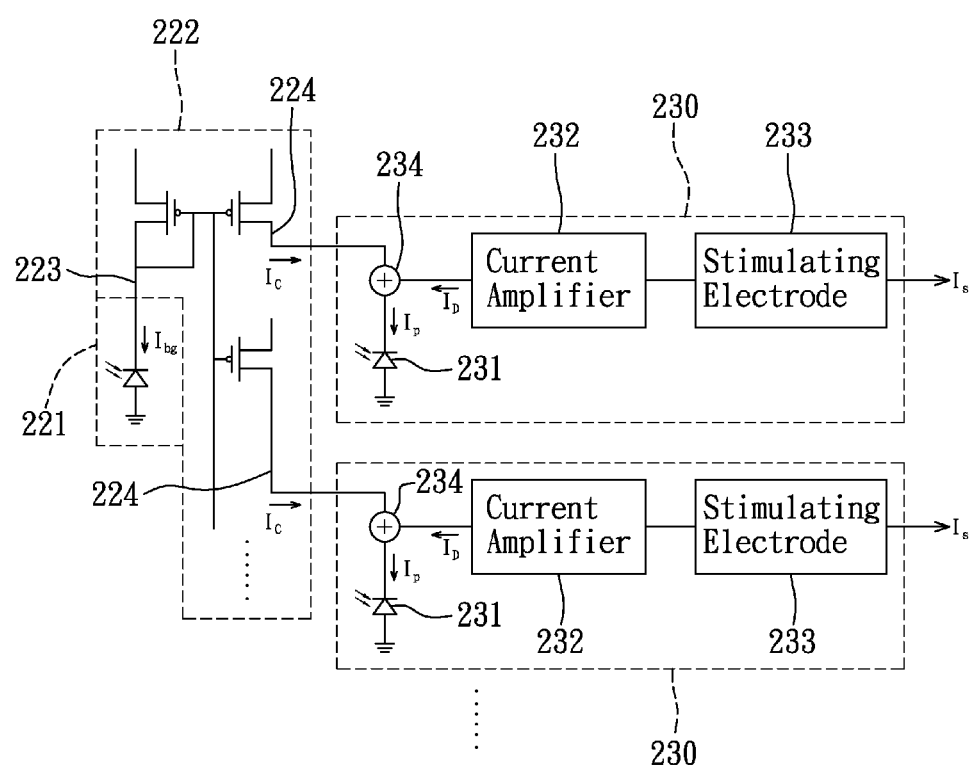
FIG. 6 is a circuit diagram showing a contrast enhancer and multiple pixels of the second preferred embodiment.

Referring to FIG. 5 and FIG. 6, the contrast enhancer 22 includes a background light sensor 221 and a current mirror 222.

The background light sensor 221 is operable to sense and convert the background light 41 into background photocurrent $I_{bg}$.

The current mirror 222 has an input end 223 coupled to the background light sensor 221 for receiving the background photocurrent $I_{bg}$, and at least one output end 224 for outputting the correction current $I_C$. The correction current $I_C$ has an amplitude corresponding to that of the background photocurrent $I_{bg}$.

The image sensing stimulator 23 includes a plurality of pixels 230. Each pixel 230 includes an image sensor 231, a correction component 234, a current amplifier 232, and a stimulating electrode 233.

The image sensor 231 is used for receiving and converting the background light 41 and a part of the target image 32 into pixel photocurrent $I_p$. The pixel photocurrents $I_p$ from the image sensors 231 of the pixels 230 serve as the initial electrical output.

The correction component 234 is coupled to the image sensor 231 and the output end 224 of the current mirror 222 for receiving the pixel photocurrent $I_p$ and the correction current $I_C$, and is operable to subtract the correction current $I_C$ from the pixel photocurrent $I_p$ so as to obtain a differential current $I_D$. Since the pixel photocurrent $I_p$ includes photocurrent generated from the target image 32 and the background light 41, with the subtraction of the correction current $I_C$, the amplitude of the differential current $I_D$ is substantially related only to the photocurrent generated from the target image 32.

The current amplifier 232 is coupled to the correction component 234 for receiving and amplifying the differential current $I_D$ therefrom.

The stimulating electrode 233 is coupled to the current amplifier 232 for receiving the differential current $I_D$ amplified thereby to output a pixel electrical stimulus $I_s$. The electrical stimuli generated by the image sensing stimulator 23 are composed of the pixel electrical stimuli $I_s$ from the pixels 230. Power for operation of the contrast enhancer 22 may be obtained from the solar cell 21 or other power sources.

The background light sensor 221 can be disposed outside the illumination range of the target image 32, so that even if the wavelengths or the polarizations of the target image 32 and the background light 41 are the same, the contrast enhancer 22 can still reduce effect of the background light 41 received by the stimulus generator 20 on the electrical stimuli generated by the image sensing stimulator 23. If the background light sensor 221 is disposed within an overlapping area of the illumination ranges of the target image 32 and the background light 41, the background light 41 provided by the background light generator 12 must have an optical characteristic (such as the wavelength, the polarization, etc.) different from that of the target image 32, and it is necessary to use an optical filter or a different type of the sensor such that the background light sensor 221 only senses the background light 41.

To sum up, in order to overcome the drawback of the conventional solar-powered artificial retina that has insufficient power source, the preferred embodiments of this invention divide functions of image sensing and power supplying among two components, and use the contrast enhancer 22 to prevent the background light 41 from interfering with the target image 32, so as to provide stable power supply while maintaining image contrast.

While the present invention has been described in connection with what are considered the most practical and preferred embodiments, it is understood that this invention is not limited to the disclosed embodiments but is intended to cover various arrangements included within the spirit and scope of the broadest interpretation so as to encompass all such modifications and equivalent arrangements.

What is claimed is:

1. An artificial retinal system comprising:
an external optical device including:
an image generator for receiving an external image, and operable to provide a target image associated with the external image and to output the target image by optical projection; and
a background light generator for providing a background light; and
a retinal implant chip including:
a solar cell to be disposed within an illumination range of the background light for receiving the background light and operable to convert the background light into electrical power; and
a stimulus generator to be disposed to receive the target image projected by said image generator and the background light provided by said background light generator, said stimulus generator being coupled to said solar cell for receiving the electrical power therefrom and including an image sensing stimulator that is operable to convert the target image into electrical stimuli, said stimulus generator further including a contrast enhancer for reducing effect of the background light received by said stimulus generator on the electrical stimuli generated by said image sensing stimulator;
wherein said contrast enhancer is to be disposed within the illumination range of the background light for receiving the background light and is operable to convert the background light into correction current;
wherein said image sensing stimulator is configured to receive and convert the target image and the background light into an initial electrical output, is coupled to said contrast enhancer for receiving the correction current therefrom, and is operable to correct the initial electrical output using the correction current so as to generate the electrical stimuli; and
wherein said contrast enhancer includes:
a background light sensor operable to sense and convert the background light into background photocurrent; and
a current mirror having an input end coupled to said background light sensor for receiving the background photocurrent, and at least one output end for outputting the correction current, the correction current having an amplitude corresponding to that of the background photocurrent; and
wherein said image sensing stimulator being coupled to said output end of said current mirror for receiving the correction current therefrom.

2. The artificial retinal system as claimed in claim 1, wherein the illumination range of the background light covers the illumination range of the target image.

3. The artificial retinal system as claimed in claim 1, wherein the amplitude of the correction current is equal to that of the background photocurrent.

4. The artificial retinal system as claimed in claim 1, wherein said background light sensor is disposed outside the illumination range of the target image.

5. The artificial retinal system as claimed in claim 1, wherein said image sensing stimulator includes a plurality of pixels, each of said pixels including:
an image sensor for receiving and converting the background light and a part of the target image into pixel photocurrent;
a correction component coupled to said image sensor and said output end of said current mirror for receiving the pixel photocurrent and the correction current, and operable to subtract the correction current from the pixel photocurrent so as to obtain a differential current;
a current amplifier coupled to said correction component for receiving and amplifying the differential current therefrom; and
a stimulating electrode coupled to said current amplifier for receiving the differential current amplified thereby to output a pixel electrical stimulus;
the pixel photocurrents from said image sensors of said pixels serving as the initial electrical output;
the electrical stimuli generated by said image sensing stimulator being composed of the pixel electrical stimuli from said pixels.

6. The artificial retinal system as claimed in claim 1, wherein the background light is infrared light, and said background light sensor includes an infrared sensor.

7. A retinal implant chip for receiving a target image and background light, said retinal implant chip comprising:
a solar cell to be disposed within an illumination range of the background light for receiving the background light and operable to convert the background light into electrical power; and a stimulus generator to be disposed to receive the target image and the background light, said stimulus generator being coupled to said solar cell for receiving the electrical power therefrom and including an image sensing stimulator that is operable to convert the target image into electrical stimuli;

wherein said stimulus generator further includes a contrast enhancer for reducing effect of the background light received by said stimulus generator on the electrical stimuli generated by said image sensing stimulator;

wherein said contrast enhancer is to be disposed within the illumination range of the background light for receiving the background light and is operable to convert the background light into correction current;

wherein said image sensing stimulator is configured to receive and convert the target image and the background light into an initial electrical output, is coupled to said contrast enhancer for receiving the correction current therefrom, and is operable to correct the initial electrical output using the correction current so as to generate the electrical stimuli;

wherein said contrast enhancer includes:

a background light sensor operable to sense and convert the background light into background photocurrent; and a current mirror having an input end coupled to said background light sensor for receiving the background photocurrent, and at least one output end for outputting the correction current, the correction current having an amplitude corresponding to that of the background photocurrent;

wherein said image sensing stimulator being coupled to said output end of said current mirror for receiving the correction current therefrom.

* * * * *